United States Patent
Han et al.

(10) Patent No.: US 6,872,679 B2
(45) Date of Patent: Mar. 29, 2005

(54) HETEROGENEOUS CATALYST REGENERATION

(75) Inventors: Yuan-Zhang Han, West Chester, PA (US); Kevin M. Carroll, Havertown, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 219 days.

(21) Appl. No.: 10/251,141

(22) Filed: Sep. 20, 2002

(65) Prior Publication Data

US 2004/0058798 A1 Mar. 25, 2004

(51) Int. Cl.[7] .......................... B01J 20/34; B01J 38/12; B01J 38/42
(52) U.S. Cl. ........................ 502/38; 502/35; 502/56
(58) Field of Search ........................... 502/35, 38, 56

(56) References Cited

U.S. PATENT DOCUMENTS

| 3,829,392 | A |   | 8/1974  | Wulff ........................ 252/430 |
| 3,923,843 | A |   | 12/1975 | Wulff ........................ 260/348.5 L |
| 4,367,342 | A |   | 1/1983  | Wulff et al. ................ 549/529 |
| 5,759,945 | A |   | 6/1998  | Carroll et al. .............. 502/242 |
| 5,798,313 | A |   | 8/1998  | Carroll et al. .............. 502/38 |
| 5,916,835 | A |   | 6/1999  | Carroll et al. .............. 502/29 |
| 5,977,009 | A | * | 11/1999 | Faraj ........................ 502/64 |
| 6,011,162 | A |   | 1/2000  | Han et al. .................. 549/529 |
| 6,114,552 | A |   | 9/2000  | Han et al. .................. 549/529 |
| 6,187,934 | B1 | * | 2/2001 | Tsuji et al. ................ 549/529 |
| 6,323,147 | B1 |   | 11/2001 | Yamamoto et al. .......... 502/64 |

FOREIGN PATENT DOCUMENTS

| EP | 0492697 A1 |   | 7/1992  |              |
| EP | 0345856    |   | 8/1992  |              |
| EP | 0323663    |   | 9/1994  |              |
| GB | 1332526    |   | 10/1973 |              |
| WO | WO 99/01445 | * | 1/1999 | ......... C07D/301/12 |

OTHER PUBLICATIONS

Castillo et al., *J. Catalysis* 161, pp. 524–529 (1996).

* cited by examiner

Primary Examiner—Stanley S. Silverman
Assistant Examiner—Jonas N. Strickland
(74) Attorney, Agent, or Firm—Kevin M. Carroll

(57) ABSTRACT

Used titanium-containing silicon oxide catalysts are regenerated by heating the used catalyst at a temperature of at least 400° C. in the presence of a oxygen-containing gas stream, followed by impregnation with a titanium source, and then calcining the impregnated catalyst to form a reactivated catalyst.

20 Claims, No Drawings

HETEROGENEOUS CATALYST REGENERATION

FIELD OF THE INVENTION

This invention relates to a method of restoring the activity of a titanium-containing silicon oxide catalyst that has been used to catalyze an oxidation reaction such as the epoxidation of an olefin with an organic hydroperoxide. Regeneration is accomplished by heating the spent heterogeneous catalyst in the presence of a gas stream comprised of oxygen, followed by impregnation of the spent catalyst with a titanium compound, then calcination.

BACKGROUND OF THE INVENTION

Many different methods for the preparation of epoxides have been developed. One such method involves the liquid-phase epoxidation of an olefin with an organic hydroperoxide in the presence of a solubilized transition metal catalyst. Although highly active and selective for olefin epoxidation, soluble catalysts must be recovered or recycled after use to avoid loss to a waste stream. However, it can be very expensive to recover the soluble catalysts after use. In addition, recycle decreases catalyst productivity by also recycling certain heavy substances such as acids and polymers that tend to accumulate along with catalyst in the heavy bottoms stream. The recycled heavies' stream decreases epoxide selectivity or olefin conversion.

Heterogeneous (insoluble) catalysts have been developed to avoid homogeneous catalyst disadvantages. U.S. Pat. No. 4,367,342 and British Pat. No. 1,332,527 disclose an olefin epoxidation process in the presence of an insoluble titania-silica catalyst comprised of an inorganic oxygen compound of titanium. Unfortunately, the disclosed catalysts have less than optimum activity and selectivity. A later-filed patent application (EP 345,856) discloses the preparation of epoxidation catalysts that are alleged to be more active than the analogous catalysts obtained by previously known procedures. EP 345,856 teaches impregnation of silica with a gaseous stream of titanium tetrachloride, followed by calcination, hydrolysis, and, optionally, silylation. Additionally, U.S. Pat. Nos. 6,011,162 and 6,114,552 disclose catalysts prepared by a liquid-phase impregnation process in a non-oxygen containing solvent.

Unfortunately, heterogeneous catalysts of the type disclosed above tend to slowly deteriorate in performance when used repeatedly or in a continuous process for a prolonged period of time. In particular, the catalyst activity (as measured by the amount of olefin or organic hydroperoxide converted per pass or in a given period of time) decreases with time to a point where continued use of the catalyst charge is no longer economically viable. Due to the relatively high cost of synthesizing this type of catalyst, regeneration of the used catalyst would be greatly preferred over replacement.

U.S. Pat. No. 5,798,313 discloses a method of restoring the activity of a used titanium-containing silicon oxide catalyst by heating the spent catalyst in the presence of a gas stream comprised of oxygen at a temperature of at least 700° C. In addition, U.S. Pat. No. 5,916,835 discloses a method of restoring the activity of a used titanium-containing silicon oxide catalyst by contacting the spent heterogeneous catalyst with one or more specific types of solvents, preferably at a moderately elevated temperature.

As with any chemical process, it is desirable to develop new and improved regeneration methods. We have discovered an effective regeneration method to restore the activity of a used titanium-containing silicon oxide catalyst.

SUMMARY OF THE INVENTION

The invention provides a method of regenerating a used titanium-containing silicon oxide catalyst. The method comprises heating the used catalyst at a temperature of at least 400° C. in the presence of an oxygen-containing gas stream, followed by impregnation of the heated used catalyst with a titanium compound, and then calcining the impregnated catalyst to form the reactivated catalyst. We surprisingly found that regeneration of used catalysts by this method resulted in a substantial activity boost as compared to the used catalyst.

DETAILED DESCRIPTION OF THE INVENTION

The catalysts regenerable by practice of the present invention are titanium-containing silicon oxide catalysts. Titanium-containing silicon oxide catalysts are well known in the art and are described, for example, in U.S. Pat. Nos. 4,367,342, 5,759,945, 6,011,162, 6114,552, 6,187,934, 6,323,147, European Patent Publication Nos. 0345856 and 0492697 and Castillo et al., *J. Catalysis* 161, pp. 524–529 (1996), the teachings of which are incorporated herein by reference in their entirety.

Such titanium-containing silicon oxide catalysts typically comprise an inorganic oxygen compound of silicon in chemical combination with an inorganic oxygen compound of titanium (e.g., an oxide or hydroxide of titanium). The inorganic oxygen compound of titanium is preferably combined with the oxygen compound of silicon in a high positive oxidation state, e.g., tetravalent titanium. The proportion of the inorganic oxygen compound of titanium contained in the catalyst composition can be varied, but generally the catalyst composition contains, based on total catalyst composition, at least 0.1% by weight of titanium with amounts from about 0.2% by weight to about 50% by weight being preferred and amounts from about 0.2% to about 10% by weight being most preferred.

One class of titanium-containing silicon oxide catalysts particularly suitable for reactivation using the methods described herein is titania-on-silica (also sometimes referred to as "$TiO_2/SiO_2$"), which comprises titanium (titanium dioxide) supported on silica (silicon dioxide). The titania-on-silica may be in either silylated or nonsilylated form.

The preparation of titania-on-silica catalysts may be accomplished by a variety of techniques known in the art. One such method involves impregnating an inorganic siliceous solid support with a titanium tetrahalide (e.g., $TiCl_4$), either by solution or vapor-phase impregnation, followed by drying and then calcination at an elevated temperature (e.g., 500° C. to 900° C.). Vapor-phase impregnation is described in detail in European Patent Pub. No. 0345856 (incorporated herein by reference in its entirety). U.S. Pat. No. 6,011,162 discloses a liquid-phase impregnation of silica using titanium halide in a non-oxygen containing solvent. In another technique, the catalyst composition is suitably prepared by calcining a mixture of inorganic siliceous solids and titanium dioxide at elevated temperature, e.g., 500° C. to 1000° C. Alternatively, the catalyst composition is prepared by cogelling a mixture of a titanium salt and a silica sol by conventional methods of preparing metal supported catalyst compositions.

The titanium-containing silicon oxide catalysts are typically utilized in oxidation reactions and are particularly useful for catalyzing the epoxidation of olefins using organic hydroperoxides. Olefin epoxidations of this type are well-known in the art and are described, for example, in U.S. Pat. No. 4,367,342.

Suitable olefins useful in epoxidation reactions include any olefin having at least one carbon-carbon double bond, and generally from 2 to 60 carbon atoms. Preferably the olefin is an acyclic alkene of from 3 to 10 carbon atoms such as propylene, butene, pentene, hexene, heptene, octene, nonene, decene, and isomers thereof. Also preferred are olefinically unsaturated compounds substituted with a hydroxyl group or a halogen group such as allyl chloride or allyl alcohol. A particularly preferred olefin is propylene.

Preferred organic hydroperoxides are hydrocarbon hydroperoxides having from 3 to 20 carbon atoms. Particularly preferred are secondary and tertiary hydroperoxides of from 3 to 15 carbon atoms, especially secondary alkyl hydroperoxides wherein the hydroperoxy group is on a carbon atom attached directly to an aromatic ring, e.g., ethylbenzene hydroperoxide. Other exemplary organic hydroperoxides suitable for use include t-butyl hydroperoxide, t-amyl hydroperoxide, cyclohexyl hydroperoxide, and cumene hydroperoxide.

In such an epoxidation process the olefin:hydroperoxide molar ratio is not particularly critical, but it is preferable to employ a molar ratio of from 1:1 up to 20:1.

The epoxidation reaction is conducted in the liquid-phase in solvents or diluents that are liquid at the reaction temperature and pressure and are substantially inert to the reactants and the products produced therefrom. In commercial practice, it will generally be most economical to use as a solvent the hydrocarbon used to produce the organic hydroperoxide reactant. For example, when ethylbenzene hydroperoxide is utilized, the use of ethylbenzene as the epoxidation solvent is preferred. It is conducted at moderate temperatures and pressures. Typically, the organic hydroperoxide is present at concentrations of from about 1 to 50 percent by weight of the epoxidation reaction mixture (including olefin). Suitable reaction temperatures vary from 0° C. to 200° C., but preferably from 25° C. to 150° C. The reaction is preferably conducted at or above atmospheric pressure. The precise pressure is not critical. The reaction mixture may, for example, be maintained substantially in a non-gaseous phase or as a two phase (gas/liquid) system. The catalyst composition, of course, is heterogeneous in character and thus is present as a solid phase during the epoxidation process of this invention. Typical pressures vary from 1 atmosphere to 100 atmospheres.

The epoxidation may be performed using any of the conventional reactor configurations known in the art for reacting olefin and organic hydroperoxide in the presence of an insoluble catalyst. Continuous as well as batch procedures may be used. For example, the catalyst may be deployed in the form of a fixed bed or slurry with provisions being made for removal of heat generated as a result of the exothermic epoxidation reaction. A fixed bed catalytic reactor adaptable for use with the present process is described in EP 323,663.

Obviously, there is no need to utilize the regeneration process of this invention until the epoxidation activity of the catalyst has diminished to an unacceptable level. Typically, however, it will be economically desirable to reactivate the catalyst when its activity is between 0.1 and 50 percent of its activity when freshly prepared, as measured by the rate at which a given hydroperoxide reacts with a given olefin. The length of time between the start of epoxidation and the point at which catalyst activity drops to a level where regeneration is to be initiated will be dependent upon many reaction parameters, including the identities of the olefin, organic hydroperoxide and solvent, the space velocities of the reactants, the reaction temperature, and the nature and amount of impurities and other changes in the catalyst associated with deactivation.

The spent titanium-containing catalyst is preferably separated in solid form from any liquid components of the reaction mixture in which it may be present prior to regeneration. For example, where the catalyst has been deployed in the form of a slurry, it may be readily collected by filtration, centrifugation, decantation, or other such mechanical means and then transferred into a vessel which is suitable for carrying out the regeneration. Alternatively, where the catalyst has been used as a fixed bed, the liquid components may be simply drained or pumped away from the spent catalyst and regeneration conducted in the same vessel as the catalytic process. If this embodiment of the regeneration process is practiced, however, the vessel employed should be constructed of materials capable of withstanding the high temperatures encountered during the regeneration. Of course, a fixed bed catalyst could also be transferred to a different vessel for regeneration purposes. It is not, however, necessary to completely dry the recovered catalyst prior to regeneration since any minor amounts of epoxidation reaction solvent, reactants, and the like adsorbed on the catalyst can be readily removed and disposed of during such regeneration. If so desired, the spent catalyst may be subjected to an initial drying step at a relatively low temperature in order to remove any volatile components present. For example, a gas stream comprised of oxygen, an inert gas, air or a mixture thereof may be passed through a fixed bed of the spent catalyst at a temperature in the range 25° C. to 200° C. The catalyst may also be exposed to subatmospheric pressure in order to facilitate the removal of volatile substances associated with the catalyst.

The spent catalyst may preferably be washed with a solvent prior to the regeneration procedure. Suitable solvents include water, alcohols, ketones, ethers, nitrites, esters, aromatic hydrocarbons, and mixtures thereof to remove substances adhering to the catalyst prior regeneration. Preferred solvents include water, $C_1$–$C_{10}$ aliphatic alcohols, $C_7$–$C_{12}$ aralkyl alcohols, $C_3$–$C_{20}$ hydrocarbons, or the like. Any conventional catalyst washing procedure is suitable. See, for example, U.S. Pat. No. 5,916,835, the teachings of which are herein incorporated by reference in its entirety. The washed catalyst may optionally be dried prior to the regeneration procedure.

The spent titanium-containing catalyst is heated in the presence of molecular oxygen at a temperature of at least 400° C., but preferably less than 1000° C. The temperature range of from 600° C. to 900° C. is especially suitable. In one embodiment of the invention, the gas stream containing oxygen is passed over the spent catalyst while the temperature (which initially may be at a relatively low temperature) is slowly elevated to a final temperature in excess of 400° C. The temperature may be kept constant during regeneration or may be periodically or continuously increased or decreased as desired. The molecular oxygen may be combined with other gases such as nitrogen and the like; the use of air is especially advantageous due to the low cost and availability of this source of oxygen. The percent molecular oxygen in the gas stream should be selected so that excessive or uncontrollable exotherms are not produced. Typically, the gas stream will comprise from about 1 to 30 volume percent oxygen. The process may be conducted such that a gas stream comprising molecular oxygen is passed over the titanium-containing catalyst in order to sweep away any volatile products evolved from the catalyst. Gas flow rates of 1 to 25 liters per kilogram of catalyst per minute have proven satisfactory. Alternatively, the regeneration may be performed in a static manner. The catalyst could also be agitated or stirred while being contacted with the oxygen-containing gas.

The catalyst is heated for such time as may be necessary to restore the desired level of activity and selectivity. Typical heating times are from 0.1 to 48 hours. The optimum time will vary somewhat depending upon the extent to which the catalyst has been deactivated, the type of reaction in which the catalyst is used, as well as other factors, but may be readily ascertained by routine experimentation.

In yet another variation of the process, the spent catalyst may be first heated to 400° C. or higher in the absence of oxygen to convert the organic impurities on the catalyst to carbon, then exposed to oxygen to burn off the carbon.

After heating the spent catalyst to at least 400° C. in the presence of an oxygen-containing gas stream, the used catalyst is then impregnated with a titanium source. Although the process of the invention is not limited by choice of a particular titanium source, preferred titanium sources include titanium compounds such as titanium alkoxides and titanium halides. Titanium chloride is especially preferred. Any conventionally employed impregnation method useful for depositing the titanium source on the spent catalyst is suitable. Particularly preferred methods include combining the spent catalyst with a solution of titanium halide in a solvent, the incipient wetness impregnation of a titanium halide solution onto the spent catalyst, or the vapor-phase impregnation using a titanium halide.

In one preferred method as described in U.S. Pat. No. 6,011,162, impregnation is performed by dissolving a titanium halide (such as $TiCl_4$) in a non-oxygenated hydrocarbon solvent and then applying the solution to the spent catalyst. Suitable solvents for this purpose are those hydrocarbons that do not contain oxygen atoms, are liquid at ambient temperatures, and are capable of solubilizing the titanium halide. Generally speaking, it will be desirable to select hydrocarbon solvents wherein titanium halide concentrations of at least 0.5 percent by weight at 25° C. can be achieved. The hydrocarbon solvent should preferably be relatively volatile so that it may be readily removed from the spent catalyst following impregnation. Solvents having normal boiling points of from 25° C. to 150° C. may advantageously be utilized. Particularly preferred classes of hydrocarbons include $C_5$–$C_{12}$ aliphatic hydrocarbons (straight chain, branched, or cyclic), $C_6$–$C_{12}$ aromatic hydrocarbons (including alkyl-substituted aromatic hydrocarbons), $C_1$–$C_{10}$ halogenated aliphatic hydrocarbons, $C_6$–$C_{10}$ halogenated aromatic hydrocarbons, and mixtures thereof. Most preferably, the solvent does not contain elements other than carbon, hydrogen, and (optionally) halogen. If halogen is present in the solvent, it is preferably chloride.

Mixtures of non-oxygenated hydrocarbons may be used, if so desired. Preferably, the solvent used for impregnation purposes is essentially free of water (i.e., anhydrous). While oxygen-containing hydrocarbons such as alcohols, ethers, esters, ketones and the like could be present in admixture with the required non-oxygenated hydrocarbon, in one desirable embodiment of the invention only non-oxygenated hydrocarbon is present as a solvent during impregnation. Examples of suitable hydrocarbon solvents include n-hexane, n-heptane, cyclopentane, methyl pentanes, methyl cyclohexane, dimethyl hexanes, toluene, xylenes, methylene chloride, chloroform, dichloroethanes, chlorobenzene, benzyl chloride, and the like.

The liquid-phase impregnation of a titanium halide is preferably characterized by the substantial exclusion of water until at least after impregnation is completed. "Substantial exclusion" in the context of this invention means that water is not deliberately added or introduced or, if deliberately added or introduced, is removed prior to introduction of titanium halide. The use of reagents and starting materials having water present at the trace levels normally and customarily found in such substances when sold on a commercial scale is within the scope of the present invention. Preferably, less than 500 ppm water (more preferably, less than 100 ppm water) is present in the non-oxygenated hydrocarbon.

Suitable titanium halides include tri- and tetra-substituted titanium complexes that have from one to four halide substituents with the remainder of the substituents, if any, being alkoxide or amino groups. Suitable titanium halides include titanium tetrachloride, titanium tetrafluoride, titanium tetrabromide, titanium tetraiodide, titanium trichloride, as well as the mixed halides of Ti(III) or Ti(IV) titanium halides, diisopropoxytitanium dichloride, bis (diethylamino)titanium dichloride, and the like. Preferably, all the substituents attached to titanium are halide. Most preferably, the titanium halide is titanium tetrachloride. While the concentration of titanium halide in the hydrocarbon solvent is not critical, the titanium halide concentration will typically be in the range of from 0.01 moles/liter to 1.0 moles/liter.

Yet another preferred impregnation method is the vapor-phase impregnation of the spent catalyst using titanium tetrachloride, as described in EP 0345856. The vapor stream is provided by flowing a gas over liquid titanium tetrachloride. The vaporization is conducted at temperatures greater than 50° C. at atmospheric pressure. Preferably, the vaporization temperature is greater than 80° C. and, most preferably, greater than 130° C. Alternatively, lower temperatures are possible by decreasing reaction pressure. Preferably, the gas is an inert gas such as nitrogen, helium, argon, carbon dioxide, and the like. The vapor stream of titanium tetrachloride is then passed over the used catalyst to complete the impregnation step. The used catalyst is maintained at a temperature greater than 50° C. during the impregnation. Preferably, the temperature of impregnation is maintained at greater than 80° C. and, most preferably, greater than 130° C.

Following impregnation, the impregnated used catalyst is then calcined by firing at an elevated temperature. Calcination may be performed in the presence of oxygen (from air, for example) or, more preferably, an inert gas which is substantially free of oxygen such as nitrogen, argon, neon, helium or the like or mixture thereof. In one embodiment of the invention, calcination is first performed in a substantially oxygen-free atmosphere with oxygen being introduced thereafter. Preferably, the calcination atmosphere contains less than 10,000 ppm mole oxygen. More preferably, less than 2000 ppm mole oxygen is present in the calcination atmosphere. Ideally, the oxygen concentration during calcination is less than 500 ppm. It is recognized, however, that substantially oxygen-free conditions are difficult to attain in large-scale commercial operations. Optionally, the calcination may be performed in the presence of a reducing gas, such as carbon monoxide, when some oxygen (e.g., up to 25,000 ppm mole) is present. The optimum amount of the reducing gas will, of course, vary depending upon a number of factors including the oxygen concentration in the calcination atmosphere and the identity of the reducing gas, but reducing gas levels of from 0.1 to 10 mole % in the calcination atmosphere are typically sufficient. In one embodiment of the invention, calcination is performed in an atmosphere comprised of oxygen, a reducing gas (preferably carbon monoxide) and, optionally, one or more inert gases (e.g., nitrogen, helium, argon, carbon dioxide).

The catalyst may be maintained in a fixed bed during calcination with a stream of gas being passed through the catalyst bed. To enhance the epoxidation activity of the catalyst, it is important that the calcination be performed at a temperature of at least 400° C. More preferably, the calcination temperature is at least 700° C. but no greater than 1000° C. Typically, calcination times of from about 0.1 to 24 hours will be sufficient.

The reactivated catalyst may be optionally reacted with water after and/or during calcination. Such reaction can be effected by, for example, contacting the catalyst with steam at an elevated temperature (preferably, a temperature in excess of 100° C., more preferably, a temperature in the range of 150° C. to 650° C.) for from about 0.1 to 6 hours. Reaction with water is desirable in order to reduce the amount of residual halide in the catalyst derived from the titanium halide reagent and to increase the hydroxy density of the catalyst.

The reactivated catalyst may also be treated with an organic silylating agent at elevated temperature. Epoxide selectivity is generally improved by silylation. Silylation is preferably performed after calcination and most preferably after both calcination and reaction with water. Suitable silylation methods adaptable for use in the present invention are described in U.S. Pat. Nos. 3,829,392 and 3,923,843 (incorporated hereby by reference in their entirety). Suitable silylating agents include organosilanes, organohalosilanes, and organodisilazanes.

Organosilanes containing from one to three organic substituents may be utilized, including, for example, chlorotrimethylsilane, dichlorodimethyl silane, nitrotrimethyl-silane, chlorotriethylsilane, chlorodimethylphenylsilane and the like. Preferred organohalosilane silylating agents include tetra-substituted silanes having from 1 to 3 halo substituents selected from chlorine, bromine, and iodine with the remainder of the substituents being methyl, ethyl, phenyl or a combination thereof.

Organodisilazanes are represented by the formula $R_3Si$—$NH$—$SiR_3$, wherein the R groups are independently hydrocarbyl groups (preferably, $C_1$–$C_4$ alkyl) or hydrogen. Especially preferred for use are the hexaalkyl substituted disilazanes such as, for example, hexamethyidisilazane.

Treatment with the silylating agent may be performed either in the liquid-phase (i.e., where the silylating agent is applied to the catalyst as a liquid, either by itself or as a solution in a suitable solvent such as a hydrocarbon) or in the vapor-phase (i.e., where the silylating agent is contacted with the catalyst in the form of a gas). Treatment temperatures are preferably in the range of from about 80° C. to 450° C., with somewhat higher temperatures (e.g., 300° C. to 425° C.) being generally preferred wherein the silylating agent is an organohalosilane and somewhat lower temperatures (e.g., 80° C. to 300° C.) being preferred for the organodisilazanes. The silylation may be carried out in a batch, semi-continuous, or continuous manner.

The length of time required for the silylating agent to react with the surface of the catalyst depends in part on the temperature and agent employed. Lower temperatures generally require longer reaction times. Generally, times of from 0.1 to 48 hours are suitable.

The amount of silylating agent employed can vary widely. Suitable amounts of silylating agent can range from about 1 percent by weight (based on the weight of the entire catalyst composition) to about 75 percent by weight, with amounts of from 2 to 50 percent by weight typically being preferred. The silylating agent can be applied to the catalyst either in one treatment or a series of treatments.

In one embodiment of the invention, the spent catalyst is contained in a suitable vessel as a fixed bed and subjected to both calcination and silylation in the same vessel. For example, the vessel is first heated to a temperature of 500° C. or higher while passing an oxygen-containing gas through the fixed bed. Once a satisfactory degree of reactivation is achieved, feed of the oxygen-containing gas is discontinued, the temperature is lowered to a temperature suitable for the silylation reaction (e.g., 100° C. to 450° C.), and the silylating agent introduced into one end of the vessel in the form of a gas and permitted to react with the catalyst surface while being passed through the fixed bed.

The regenerated catalyst which has been reactivated in accordance with the process of the invention may be admixed with freshly prepared catalyst prior to reuse, if so desired, or used directly.

The following examples merely illustrate the invention. Those skilled in the art will recognize many variations that are within the spirit of the invention and scope of the claims.

EXAMPLE 1

Fresh and Used Catalyst

Fresh catalyst is prepared according to Example 8A in U.S. Pat. No. 6,011,162. Catalyst 1A contains 2.6 wt. % titanium and is composed of granular particles with size ranging from 0.6 to 1.4 mm in diameter. Catalyst 1A is used in the epoxidation of propylene with EBHP oxidate in a fixed bed reactor until the catalyst has lost approximately 97% of its original activity. Following propylene epoxidation, the spent catalyst is removed from the reactor and air-dried. The spent catalyst is designated as Catalyst 1B.

EXAMPLE 2

Catalyst Regeneration

Catalyst Washing

The used catalyst 1B (22 g) is mixed with 40 mL of methanol, and the slurry is charged into a 1 inch ID glass column. The used catalyst is washed by passing methanol (an additional 100 mL) over the bed of used catalyst, followed by a water wash (125 mL water), and another methanol wash (40 mL). The washed catalyst is then transferred to a 3-neck flask and dried at 120° C. under nitrogen flow. The washed material is designated as Catalyst 2A.

Heating, Ti Addition, and Calcination

A portion of Catalyst 2A is heated in air atmosphere in a furnace at 550° C. for 4 hours. The heated material is then impregnated by adding a solution containing titanium tetrachloride (1.04 g) in n-heptane (50 mL) to the heated material (7.95 g) under dry inert gas atmosphere. The mixture is mixed well by swirling. The solvent is removed by heating the flask in an oil batch at temperature of 125° C. under nitrogen flow for 1.5 hours. The impregnated material is calcined at 850° C. under nitrogen flow, steamed at 400° C., then silylated with hexamethyldisilazane in a procedure similar to that described in Example 8A of U.S. Pat. No. 6,011,162. The regenerated catalyst is designated as Catalyst 2B.

EXAMPLE 3

Effect of Added Titanium to Fresh Catalyst

Catalyst 3A: Silica (Grace Davison DAVICAT P-732, particle size 0.6–1.4 mm, surface area 300 m²/g) is dried at 400° C. in air for 4 hours and cooled to room temperature. The dried silica (39.62 g) is charged into a 500-mL 3-neck round-bottom flask equipped with an inert gas inlet, a gas outlet, and a scrubber containing aqueous sodium hydroxide solution. A solution consisting of 84.21 g n-heptane (99+%, water <50 ppm) and 5.02 g titanium (IV) tetrachloride is added to the silica under dry inert gas atmosphere. The mixture is mixed well by swirling. The solvent is removed by heating the flask in an oil batch at temperature of 125° C. under nitrogen flow for 1.5 hours.

A portion of the above material (35 g) is charged into a tubular quartz reactor (1 inch ID, 16 inch long) equipped with a thermowell, a 500 mL 3-neck round-bottom flask, a heating mantle, an inert gas inlet, and a scrubber (containing sodium hydroxide solution). The catalyst bed is heated to 850° C. under dry nitrogen (99.999%) flow (400 cc/min). After the bed is maintained at 850° C. for 30 minutes, the power to the furnace is turned off and the catalyst bed is cooled down to 400° C.

Water (3.0 g) is added into the 3-neck round-bottom flask and the flask is heated with a heating mantle to reflux while keeping the nitrogen flow at 400 cc/min. The water is distilled through the catalyst bed over a period of 30 minutes. A heat gun is used to heat the round-bottom flask to make sure that any residual water is driven out of the flask through the bed. The bed is maintained at 400° C. for an additional 2 hours. The tube reactor is cooled to room temperature. The non-silylated catalyst is designated as Catalyst 3. A portion of Catalyst 3 is further silylated as following to make Catalyst 3A. Another portion of the material is used to make Catalyst 3B.

A 500-mL 3-neck round-bottom flask is equipped with a condenser, a thermometer, and an inert gas inlet. The flask is charged with 39 g heptane (water <50 ppm), 3.10 g hexamethyldisilazane and 11.8 g of the nonsilylated catalyst. The system is heated with oil bath to reflux (98° C.) under inert atmosphere and kept refluxing for 2 hours. The system is cooled down under inert gas atmosphere and the catalyst is filtered and washed with heptane (100 mL). The material is then dried in a flask under inert gas flow at 180–200° C. for 2 hours. Catalyst 3A is obtained, and analyzes for 3.5 wt. % Ti and 1.97 wt. % C.

Catalyst 3B: A portion of non-silylated Catalyst 3 is impregnated again with TiCl$_4$ according to the procedure above for Catalyst 3A. Catalyst 3 (27 g) is used in place of silica. The impregnation of TiCl$_4$ is performed using a solution consisting of 60 g n-heptane (99+%, water <50 ppm) and 3.46 g titanium (IV) tetrachloride. The calcination and hydration steps are performed according to the above procedure. The silylation step is performed using 58 g heptane (water <50 ppm), 6.1 g hexamethyldisilazane and 25 g of the nonsilylated catalyst. The resulting Catalyst 3B analyzed for 5.4 wt. % Ti and 2.0 wt. % C.

EXAMPLE 4

Batch Epoxidation of 1-octene with EBHP Oxidate at 50° C.

To evaluate the performance of the catalysts prepared in Examples 1, 2 and 3, batch epoxidations of 1-octene using ethylbenzene hydroperoxide are carried out. The following procedure is employed.

A feed solution is prepared by mixing 220 g 1-octene, 50 g EBHP oxidate (containing 35% EBHP), and 10 g nonane (internal standard). A portion of the feed solution (28 g) is transferred under inert atmosphere to a 4-neck 100 mL round bottom flask attached to a condenser, a thermocouple, a stirrer bar, and a sampling port. The mixture is heated to 50° C., while stirring (with a stir bar) at a rate of 700 rpm. The catalyst (0.2 g) is then added to the flask and the mixture is heated for 30 minutes at 50° C. A product sample (3 mL) is taken 30 minutes after catalyst addition. Both the feed sample and the product sample are analyzed by GC for EBHP and epoxyoctane concentrations. Conversion and epoxide selectivity are calculated relative to hydroperoxide consumed. First order activity (k) is calculated by the equation k=−[ln(1−% conversion)].

The results, shown in Table 1, show that full regeneration restores about half of the activity of the original catalyst. Washing restores very little activity. Comparative examples 3A and 3B demonstrate that the increased activity by the full regeneration route is not due to the increased titanium loading. As seen in comparative examples 3A and 3B, an increase in titanium loading has no effect on catalyst activity.

TABLE 1

COMPARISON OF CATALYST ACTIVITY

| Catalyst | Support Surface Area (m²/g) | Ti loading (wt. %) | EBHP Conversion (%) | Epoxide Selectivity (%) | k |
|---|---|---|---|---|---|
| 1A | Fresh | 2.6 | 50 | 91 | 0.69 |
| 1B | Used | 2.1 | 2 | — | 0.02 |
| 2A* | Washed | 2.1 | 4 | — | 0.04 |
| 2B | Full Regeneration | 5.0 | 28 | 92 | 0.32 |
| 3A* | Fresh | 3.5 | 51 | 92 | 0.71 |
| 3B* | Fresh | 5.4 | 51 | 92 | 0.71 |

*Comparative Example

We claim:

1. A method of regenerating a used titanium-containing silicon oxide catalyst comprising the steps of:
    (a) heating the used catalyst at a temperature of at least 400° C. in the presence of a gas stream comprised of oxygen to obtain a heated product;
    (b) impregnating the heated product of step (a) with a titanium source to obtain an impregnated product; and
    (c) calcining the impregnated product of step (b) to form a reactivated catalyst.

2. The method of claim 1 comprising the additional step of washing the used titanium-containing silicon oxide catalyst with a solvent prior to step (a).

3. The method of claim 1 wherein the used catalyst is heated at a temperature greater than about 600° C.

4. The method of claim 1 wherein air is used as the gas stream.

5. The method of claim 1 wherein the titanium source is selected from the group consisting of:
    (a) a solution of a titanium halide in a non-oxygenated hydrocarbon solvent; and
    (b) a vapor stream of titanium tetrachloride.

6. The method of claim 5 wherein the titanium halide is titanium tetrachloride.

7. The method of claim 5 wherein the non-oxygenated hydrocarbon solvent is selected from the group consisting of $C_5$–$C_{12}$ aliphatic hydrocarbons, $C_6$–$C_{12}$ aromatic hydrocarbons, $C_1$–$C_{10}$ halogenated aliphatic hydrocarbons, $C_6$–$C_{10}$ halogenated aromatic hydrocarbons, and mixtures thereof.

8. The method of claim 1 wherein calcination step (c) is performed at a temperature of at least 500° C.

9. The method of claim 1 wherein calcination step (c) is performed in a substantially oxygen-free atmosphere.

10. The method of claim 1 comprising at least one additional step (d) or (e) following step (c):
   (d) heating the reactivated catalyst in the presence of water; or
   (e) reacting the reactivated catalyst with an organic silylating agent to form a silylated activated catalyst.

11. The method of claim 1 wherein the used titanium-containing silicon oxide catalyst has been used to catalyze epoxidation of an olefin using an organic hydroperoxide.

12. The method of claim 1 comprising an initial step prior to step (a) wherein the used catalyst is heated at a temperature of at least 400° C. in the absence of oxygen.

13. The method of claim 1 wherein the titanium-containing silicon oxide catalyst excludes catalysts having a zeolite-type structure.

14. A method of regenerating a used titanium-containing silicon oxide catalyst comprising the steps of:
   (a) heating the used catalyst at a temperature of at least 400° C. in the presence of a gas stream comprised of oxygen to obtain a calcined product;
   (b) impregnating the calcined product of step (a) with a titanium source selected from the group consisting of:
      (1) a solution of a titanium halide in a non-oxygenated hydrocarbon solvent; and
      (2) a vapor stream of titanium tetrachloride;
      to obtain an impregnated product;
   (c) calcining the impregnated product of step (b) to form a reactivated catalyst; and
   (d) reacting the reactivated catalyst with an organic silylating agent to form a silylated activated catalyst.

15. The method of claim 14 comprising an additional step of washing the used catalyst with a solvent selected from the group consisting of water and aliphatic alcohols prior to step (a).

16. The method of claim 14 wherein the organic silylating agent is selected from the group consisting of organohalosilanes, organosilylamines, organodisilazanes, and mixtures thereof.

17. The method of claim 16 wherein the organic silylating agent is an organodisilazane.

18. The method of claim 14 wherein the used catalyst has been used to catalyze epoxidation of propylene using an organic hydroperoxide.

19. The method of claim 14 comprising an initial step prior to step (a) wherein the used catalyst is heated at a temperature of at least 400° C. in the absence of oxygen.

20. The method of claim 14 wherein calcination step (c) is performed in a substantially oxygen-free atmosphere.

* * * * *